United States Patent
Palmer et al.

(10) Patent No.: US 9,468,770 B2
(45) Date of Patent: Oct. 18, 2016

(54) RANDOM-ACCESS ELECTRODE ADDRESSING SYSTEMS AND METHODS

(75) Inventors: Logan P. Palmer, Santa Monica, CA (US); Ji-Jon Sit, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 9 days.

(21) Appl. No.: 14/412,182

(22) PCT Filed: Jul. 13, 2012

(86) PCT No.: PCT/US2012/046753
§ 371 (c)(1),
(2), (4) Date: Dec. 30, 2014

(87) PCT Pub. No.: WO2014/011188
PCT Pub. Date: Jan. 16, 2014

(65) Prior Publication Data
US 2015/0328471 A1    Nov. 19, 2015

(51) Int. Cl.
*A61N 1/36* (2006.01)
*A61N 1/372* (2006.01)
*A61N 1/05* (2006.01)

(52) U.S. Cl.
CPC ......... *A61N 1/37252* (2013.01); *A61N 1/0541* (2013.01); *A61N 1/36032* (2013.01)

(58) Field of Classification Search
None
See application file for complete search history.

(56) References Cited

U.S. PATENT DOCUMENTS

| | | |
|---|---|---|
| 3,727,616 A | 4/1973 | Lenzkes |
| 3,888,261 A | 6/1975 | Maurer |
| 4,019,518 A | 4/1977 | Maurer et al. |
| 4,408,608 A | 10/1983 | Daly et al. |
| 4,532,930 A | 8/1985 | Crosby et al. |
| 4,612,934 A | 9/1986 | Borkan |
| 5,603,726 A | 2/1997 | Schulman et al. |
| 6,157,861 A | 12/2000 | Faltys et al. |
| 6,219,580 B1 | 4/2001 | Faltys et al. |
| 7,127,298 B1 | 10/2006 | He et al. |
| 7,333,858 B2 | 2/2008 | Killian et al. |
| 7,382,850 B2 | 6/2008 | Zierhofer |
| 7,571,005 B1 | 8/2009 | Segel et al. |
| 7,941,223 B2 | 5/2011 | Zierhofer et al. |
| 2005/0195930 A1 | 9/2005 | Spital et al. |
| 2006/0235490 A1 | 10/2006 | Killian et al. |

(Continued)

FOREIGN PATENT DOCUMENTS

CN    101347367    2/2011

OTHER PUBLICATIONS

International Search Report and Written Opinion received in International Application No. PCT/US12/046753, dated May 24, 2013.

*Primary Examiner* — Kennedy Schaetzle
(74) *Attorney, Agent, or Firm* — ALG Intellectual Property, LLC

(57) ABSTRACT

An exemplary cochlear implant includes a communication facility configured to receive at least a first data word and a second data word in series from a sound processor by way of a forward-telemetry link and a processing facility communicatively coupled to the communication facility and configured to 1) use the first data word to dynamically determine an address associated with an electrode by way of which a stimulation pulse is to be applied during a time slot of a stimulation frame and 2) use the second data word to determine an amplitude of the stimulation pulse that is to be applied by way of the electrode during the time slot of the stimulation frame. Corresponding systems and methods are also disclosed.

20 Claims, 8 Drawing Sheets

(56) References Cited

U.S. PATENT DOCUMENTS

2009/0024184 A1 1/2009 Sun et al.
2011/0004274 A1 1/2011 Schleich et al.
2012/0083859 A1 4/2012 Sun et al.

RANDOM-ACCESS ELECTRODE ADDRESSING SYSTEMS AND METHODS

BACKGROUND INFORMATION

Conventional cochlear implant systems include a sound processor configured to be located external to a patient (e.g., behind the ear) and a cochlear implant configured to be implanted within the patient. In this configuration, the sound processor may process audio signals presented to the patient and wirelessly transmit stimulation parameters to the cochlear implant so that the cochlear implant may generate and apply stimulation pulses representative of the audio signals to the patient by way of a plurality of electrodes implanted within the patient. For example, the sound processor may transmit a forward telemetry sequence comprising a series of electrode-specific amplitude words to the cochlear implant, which may then process the amplitude words to derive the amplitude of the stimulation pulses to be applied by way of the electrodes.

Conventional cochlear implant systems require the electrode-specific amplitude words to be transmitted in a predetermined order. For example, if a particular cochlear implant system has sixteen total electrodes (electrodes E1 through E16), the sound processor included in the cochlear implant system may be required to transmit the electrode-specific amplitude words to the cochlear implant in sequential order (i.e., by transmitting the amplitude word specific to electrode E1, followed by the amplitude word specific to electrode E2, and so on until the amplitude word specific to electrode E16 is transmitted) or in any other predetermined order.

Unfortunately, the order in which the amplitude words are transmitted cannot be dynamically changed during stimulation. This becomes problematic when it is desirable to skip certain electrodes during a particular stimulation frame (e.g., in accordance with an N of M stimulation strategy). In these cases, a "skip" command associated with a particular electrode (i.e., a command configured to direct the cochlear implant to not apply stimulation pulses by way of the electrode) may be transmitted in place of an amplitude word for the electrode. However, the skip command still occupies a time slot in the forward telemetry sequence and thus slows down the overall stimulation rate that could be achieved by not transmitting the skip command

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
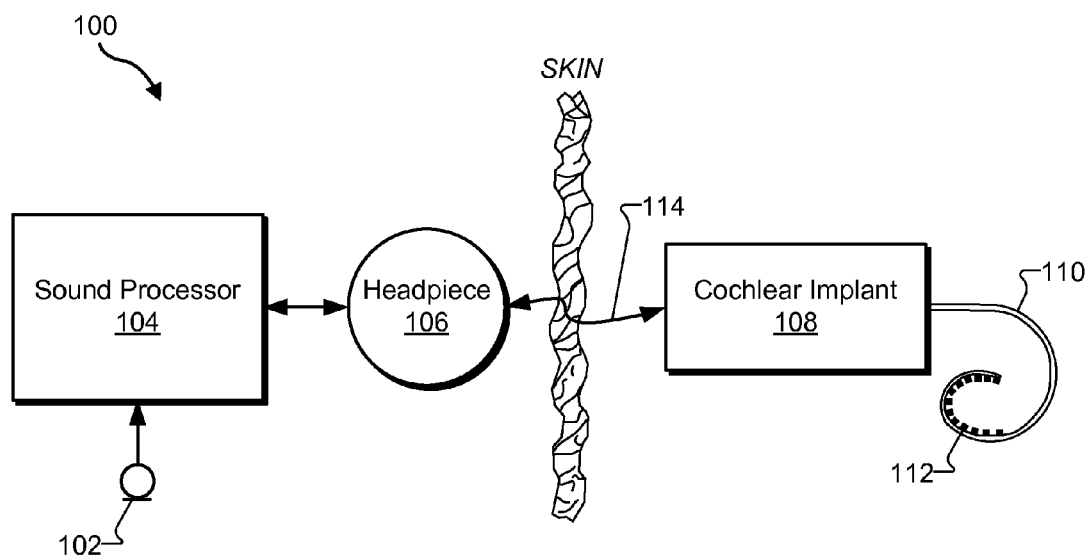
FIG. 1 illustrates an exemplary cochlear implant system according to principles described herein.

Random-access electrode addressing systems and methods are described herein. As will be described below, a cochlear implant may include a communication facility configured to receive at least a first data word and a second data word in series from a sound processor by way of a forward-telemetry link and a processing facility communicatively coupled to the communication facility and configured to 1) use the first data word to dynamically determine an address associated with an electrode by way of which a stimulation pulse is to be applied during a time slot of a stimulation frame and 2) use the second data word to determine an amplitude of the stimulation pulse that is to be applied by way of the electrode during the time slot of the stimulation frame.

The systems and methods described herein may facilitate dynamic addressing (i.e., selection of) electrodes during a stimulation frame. In this manner, a cochlear implant system may not be limited to stimulating electrodes in a fixed order or to dedicating a transmission time slot to each electrode in a forward telemetry sequence transmitted from the sound processor to the cochlear implant. This, in turn, may allow the cochlear implant system to skip certain electrodes during a stimulation frame without dedicating transmission time slots in the forward telemetry sequence to those electrodes, which may improve an overall stimulation rate of the cochlear implant system.

To illustrate, a particular cochlear implant system may include a total of sixteen electrodes and may be configured to operate in accordance with an N of M stimulation strategy that specifies that electrical stimulation is to be applied to only five of the sixteen electrodes during a particular stimulation frame. If a fixed electrode addressing heuristic is used (i.e., a heuristic that dedicates a transmission time slot in the forward telemetry sequence to each of the sixteen electrodes regardless of whether they are stimulated during the stimulation frame), sixteen data words (i.e., five words that specify amplitudes for the stimulation pulses to be applied by way of the five electrodes and eleven words that specify that the remaining eleven electrodes are to be skipped during the stimulation frame) are required to be in the forward telemetry sequence. This results in an overall stimulation rate of sixteen forward telemetry words per frame. However, if a dynamic electrode addressing heuristic in accordance with the systems and methods described herein is used, a total of ten data words are required to be in the forward telemetry sequence (i.e., five data words that specify addresses of the five electrodes and five data words that specify amplitudes for the stimulation pulses to be applied by way of the five electrodes). This results in an overall stimulation rate of ten forward telemetry words per frame, a sixty percent improvement compared to the overall stimulation rate associated with the fixed electrode addressing heuristic.

The systems and methods described herein may also reduce the timing resolution that can be achieved to activate any given electrode at a certain time. To illustrate, a cochlear implant system may include sixteen electrodes and operate in accordance with a fixed electrode addressing heuristic. In this example, the best timing resolution that can be achieved using the fixed electrode addressing heuristic is 16 T because the cochlear implant system must cycle through all sixteen time slots associated with the sixteen electrodes before it can return to stimulate a particular electrode again. In contrast, if a dynamic electrode addressing heuristic in accordance with the systems and methods described herein is used, the timing resolution is improved to 2 T because the same electrode can be repeatedly stimulated.

As used herein, a "stimulation frame" refers to a time period during which one or more stimulation pulses are applied by way of one or more electrodes. A stimulation frame may be divided into a number of "time slots" during which each stimulation pulse is applied.

As used herein, a "forward telemetry sequence" refers to a sequence of data words that are transmitted serially by a sound processor to a cochlear implant. The time period associated with transmitting each data word in a forward telemetry sequence is referred to herein as a "transmission time slot."

FIG. 1 illustrates an exemplary cochlear implant system 100. Cochlear implant system 100 may include a microphone 102, a sound processor 104, a headpiece 106 having a coil 108 disposed therein, a cochlear implant 108, and a lead 112 with a plurality of electrodes 110 disposed thereon. Additional or alternative components may be included within cochlear implant system 100 as may serve a particular implementation.

As shown in FIG. 1, microphone 102, sound processor 104, and headpiece 106 may be located external to a cochlear implant patient. In some alternative examples, microphone 102 and/or sound processor 104 may be implanted within the patient. In such configurations, the need for headpiece 106 may be obviated.

Microphone 102 may detect an audio signal and convert the detected signal to a corresponding electrical signal. The electrical signal may be sent from microphone 102 to sound processor 104 via a communication link 112, which may include a telemetry link, a wire, and/or any other suitable communication link.

Sound processor 104 is configured to direct cochlear implant 108 to generate and apply electrical stimulation (e.g., one or more stimulation pulses) representative of one or more audio signals (e.g., one or more audio signals detected by microphone 102, input by way of an auxiliary audio input port, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108. Sound processor 104 may include or be implemented by a behind-the-ear ("BTE") unit, a body worn device, an electro-acoustic stimulation ("EAS") device, and/or any other sound processing unit as may serve a particular implementation.

In some examples, sound processor 106 may wirelessly transmit stimulation parameters (e.g., in the form of data words included in a forward telemetry sequence) and/or power signals to cochlear implant 108 by way of a wireless communication link 114 between headpiece 106 and cochlear implant 108. It will be understood that communication link 114 may include a bi-directional communication link and/or one or more dedicated uni-directional communication links.

Headpiece 106 may be communicatively coupled to sound processor 104 and may include one or more interface components configured to facilitate selective wireless coupling of sound processor 104 to cochlear implant 108. Headpiece 106 may be additionally or alternatively be used to selectively and wirelessly couple any other external device to cochlear implant 108. To this end, headpiece 106 may be configured to be affixed to the patient's head and positioned such that a coil housed within headpiece 106 is communicatively coupled to a corresponding coil included within or otherwise associated with cochlear implant 108. In this manner, stimulation parameters and power signals may be wirelessly transmitted between sound processor 104 and cochlear implant 108 via communication link 114.

Cochlear implant 108 may include any type of implantable stimulator that may be used in association with the systems and methods described herein. For example, cochlear implant 108 may include an implantable cochlear stimulator. In some alternative implementations, cochlear implant 108 may include a brainstem implant and/or any other type of cochlear implant that may be implanted within a patient and configured to apply stimulation to one or more stimulation sites located along an auditory pathway of a patient.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites within the patient via one or more electrodes 112 disposed along lead 110. In some examples, cochlear implant 108 may include a plurality of independent current sources each associated with a channel defined by one or more of electrodes 112. In this manner, different stimulation current levels may be applied to multiple stimulation sites simultaneously by way of multiple electrodes 112. In such examples, cochlear implant system 100 may be referred to as a "multi-channel cochlear implant system."

Figure 2:
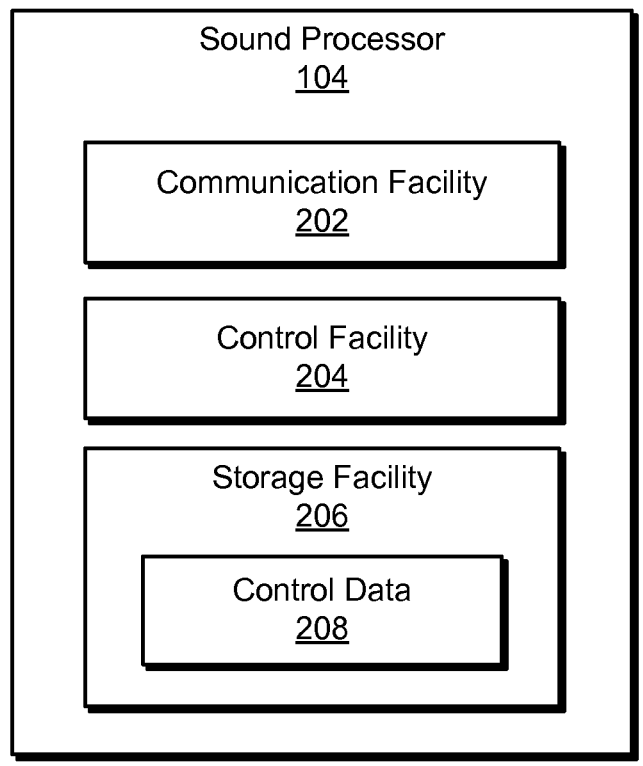
FIG. 2 illustrates exemplary components of a sound processor according to principles described herein.

FIG. 2 illustrates exemplary components of sound processor 104. As shown in FIG. 2, sound processor 104 may include a communication facility 202, a control facility 204, and a storage facility 206, which may be in communication with one another using any suitable communication technologies. Each of these facilities may include any combination of hardware, software, and/or firmware as may serve a particular application. For example, one or more of facilities 202-206 may include a computing device or processor configured to perform one or more of the functions described herein. Facilities 202-306 will now be described in more detail.

Communication facility 202 may be configured to facilitate communication between sound processor 104 and cochlear implant 108. For example, communication facility 202 may include one or more components configured transmit forward telemetry data (e.g., a forward telemetry sequence comprising a series of data words) configured to direct cochlear implant 108 to generate and apply electrical stimulation representative of one or more audio signals by way of one or more electrodes 112. Communication facility 202 may be further configured to receive data (e.g., back telemetry data) from cochlear implant 108.

Control facility 204 may be configured to control an operation of cochlear implant 108. For example, control facility 204 may control cochlear implant 108 by generating data words and then directing communication facility 202 to transmit the data words to cochlear implant 108. As will be described below, the data words may include one or more address words and/or one or more amplitude words. As used herein, an "address word" is configured to indicate an address of a particular electrode by way of which a stimulation pulse is to be applied. An "amplitude word" is configured to indicate an amplitude of one or more stimulation pulses that are to be applied by way of a particular electrode. Each data word may include any number of bits as may serve a particular implementation. For example, each data word may include at least four bits. Exemplary data words that may be transmitted by sound processor 104 to cochlear implant 108 will be described in more detail below.

Storage facility 206 may be configured to maintain control data 208 representative of one or more types of control data (e.g., one or more data words) that may be transmitted to cochlear implant 108. Storage facility 206 may be configured to maintain additional or alternative data as may serve a particular implementation.

Figure 3:
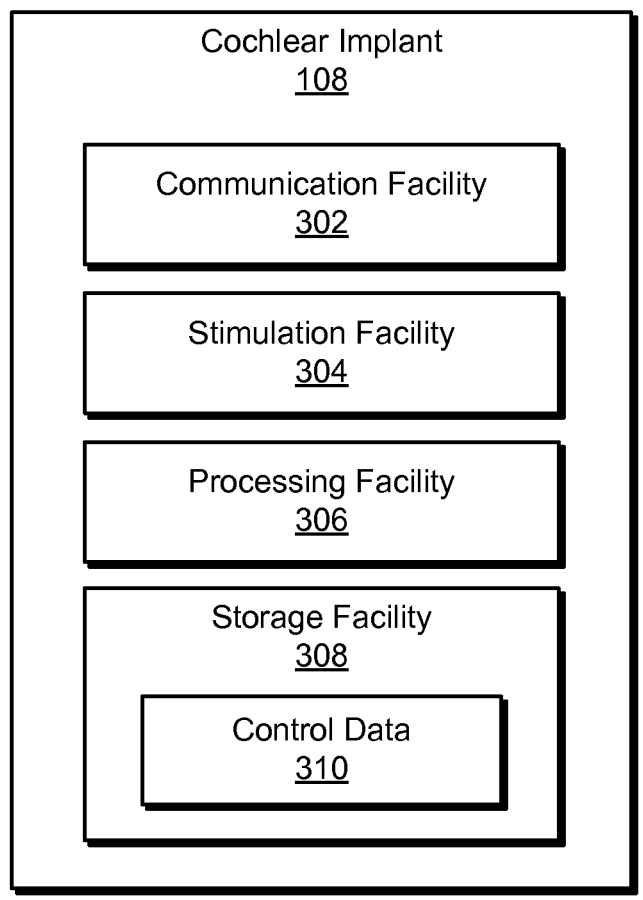
FIG. 3 illustrates exemplary components of a cochlear implant according to principles described herein.

FIG. 3 illustrates exemplary components of cochlear implant 108. As shown in FIG. 3, cochlear implant 108 may include a communication facility 302, a stimulation facility 304, a processing facility 306, and a storage facility 308, which may be in communication with one another using any suitable communication technologies. Each of these facilities may include any combination of hardware, software, and/or firmware as may serve a particular application. For example, one or more of facilities 302-308 may include a computing device or processor configured to perform one or more of the functions described herein. Facilities 302-308 will now be described in more detail.

Communication facility 302 may be configured to facilitate communication between cochlear implant 108 and sound processor 104. For example, communication facility 302 may include or be in communication with one or more coils configured to receive control data (e.g., a forward telemetry sequence that includes a series of data words) and/or power signals from sound processor 104 (e.g., by way of communication link 114). Communication facility 302 may additionally or alternatively be configured to transmit one or more status signals and/or other data to sound processor 104.

Stimulation facility 304 may be configured to generate and apply stimulation current (e.g., one or more stimulation pulses) by way of one or more electrodes 112 in accordance with control data received from sound processor 104. To this end, current generation facility 306 may include one or more current generators and/or any other circuitry configured to facilitate generation of stimulation current. For example, current generation facility 306 may include an array of independent current generators each corresponding to a distinct electrode or channel.

Processing facility 306 may be configured to process control data and/or power signals received from sound processor 104. For example, communication facility 302 may receive a first data word and a second data word in series from sound processor 104 by way of a forward-telemetry link (e.g., communication link 114). Processing facility 306 may use the first data word to dynamically determine an address associated with an electrode by way of which a stimulation pulse is to be applied during a time slot of a stimulation frame, and use the second data word to determine an amplitude of the stimulation pulse that is to be applied by way of the electrode during the time slot of the stimulation frame. This and other examples of processing data words provided by sound processor 104 will be described in more detail below.

Storage facility 308 may be configured to maintain control data 310 received from sound processor 104. Storage facility 308 may be configured to maintain additional or alternative data as may serve a particular implementation.

Figure 4:
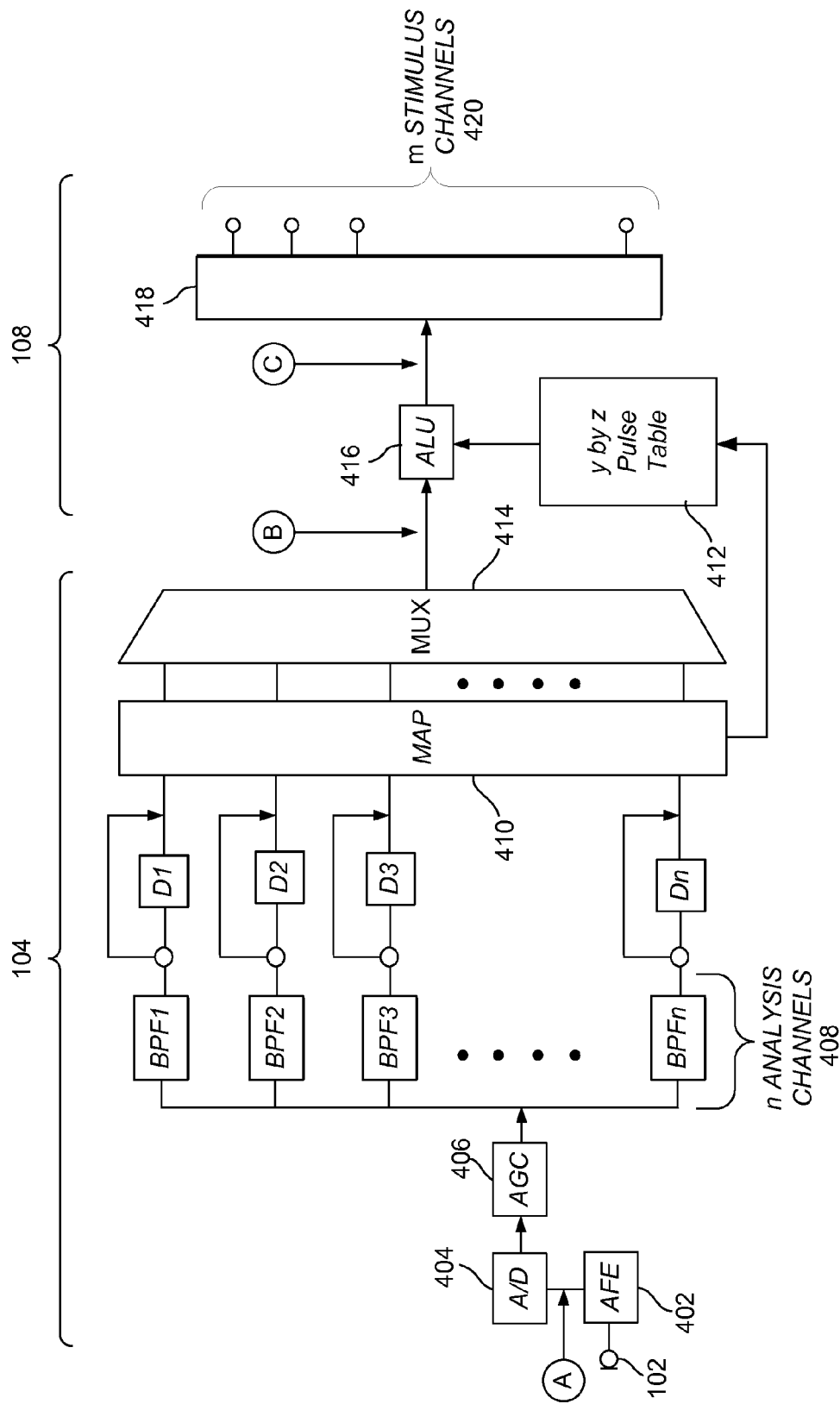
FIG. 4 illustrates an exemplary functional block diagram of a sound processor and a cochlear implant according to principles described herein.

FIG. 4 illustrates an exemplary functional block diagram of sound processor 104 and cochlear implant 108. The various functions illustrated in FIG. 4 may be performed by any of the facilities described herein. FIG. 4 is more fully described in U.S. Pat. No. 6,219,580, the contents of which are incorporated herein by reference in their entirety.

In FIG. 4, it is seen that a microphone 102 senses acoustical information and converts it to electrical signals. These signals are then amplified in audio front-end (AFE) circuitry 402. The amplified audio signal, at point (A) in FIG. 4, is then converted to a digital signal by analog-to-digital (A/D) converter 404. The resulting digital signal is then subjected to automatic gain control (AGC) processing using a suitable AGC unit 406. The function of the AGC unit 406 is to compress the dynamic range of the speech signals so as to provide a more consistent overall level of stimulus to the electrodes, as well as to equalize the level between close and more distant speakers in a given area, e.g., within a room.

As further seen in FIG. 4, after signal processing by the AGC unit 406, the signal is processed in one of a plurality of analysis channels 408. For example, eight separate analysis channels 408 may be used, each responding to a different frequency content of the sensed acoustical signal. In other words, the incoming signal is divided into a multiplicity of n frequency channels, as defined by a bank of respective bandpass or other filters BPF1, BPF2, BPF3, . . . BPFn. The lowest frequency filter may be a lowpass filter, and the highest frequency filter may be a high-pass filter.

After the received signal is filtered, it passes through a respective detection stage D1, D2, D3, . . . Dn. As its name implies, the detection stage involves some type of energy detection circuit, which may be realized, e.g., through a rectification circuit followed by an integrator circuit. The rectification may be either full-wave, or half-wave. Full-wave rectification provides a more spectrally pure signal than half-wave, but the spiral ganglion nerve cells, under certain conditions, seem to perform a type of half-wave rectification. Other types of energy-detection stages could also be used, e.g., a simple envelope detector.

After energy detection, or bypassing of such, the signal from each of the n analysis channels is forwarded to a mapping stage 410. The mapping stage 410 performs additional processing of the signal, as required. More particularly, the mapping stage 410 may split the signal into two paths. In a first path, the signal is compared to a reference threshold signal, and if the threshold is exceeded, then that information is forwarded to a pulse table 412 for use with certain pulsatile speech processing strategies. The function of the pulse table 412 is explained more fully below. In a second path, the additional processing includes signal compression, pursuant to any suitable signal compression unit. The compressed signal is then mapped between the patient's threshold and most comfortable levels, and/or between other set levels. A volume function is also implemented in conjunction with the compression and mapping function.

After compression and mapping in the mapping stage 410, the n analysis channels are serialized through a multiplexer 414, or equivalent circuitry, into one serial data channel, present at point (B) in FIG. 4. As the data stream passes through the serial data channel, it is acted upon by data from the pulse table 412 in an arithmetic logic unit (ALU) 416. The operation performed by the ALU 416 is usually a simple multiplication, at least with respect to pulsatile strategies. The result of this multiplication is a "product" signal, present at point (C) in FIG. 4. This product signal represents a control signal that is then passed through to a pulse generator 418, where it is used to control the precise stimulation currents that are delivered through each of m stimulus channels 420.

Pulse table 412 is effectively an y by z table, having y columns and z rows, or the equivalent. As the serial data stream passes through point (B), it effectively represents, in appropriate time increments, a yx1 matrix, or data word. As this yx1 matrix, or word, is acted upon in the ALU 416 by the y by z table, the result is an zx1 data matrix, or data word, for each of the y columns of the table. These y zx1 words pass through point (C) in the data path and are applied, one word at a time, to each of the m stimulus channels in order to control the stimulus current at each of the m stimulus channels. In this manner, the complex spatiotemporal current stimulation patterns associated with the selected speech processing strategy is applied to the auditory nerve through the patient's cochlea.

In the manner described above, each of the n analysis channels may be mapped to one or more stimulus channels. That is, it is seen that the system as configured in FIG. 4 provides a multiplicity of channels, n, wherein the incoming signal is analyzed. The information contained in these n "analysis channels" is then appropriately processed, compressed and mapped in order to control the actual stimulus patterns that will be applied to the patient by the pulse generator 418 and its associated electrodes 112.

Any of the functions and/or components shown in FIG. 4 may be implemented by sound processor 104 and/or cochlear implant 108. For example, as shown in FIG. 4, AFE circuitry 402, A/D converter 404, AGC unit 406, analysis channels 408, detection stages D1-Dn, mapping stage 410, and MUX 414 may be implemented by sound processor 104. ALU 416, pulse table 412, and pulse generator 418 may be implemented by cochlear implant 108.

As mentioned, sound processor 104 may dynamically specify an order in which stimulation pulses are applied by way of electrodes 112. To illustrate, an example in which an N of M stimulation strategy that employs current steering between adjacent pairs of electrodes is used will now be described in connection with FIG. 5. In this example, N is equal to four and M is equal to sixteen. In other words, stimulation pulses are to be applied by way of four of sixteen total electrode channels (wherein each electrode channel includes two electrodes) during a particular stimulation frame.

Figure 5:
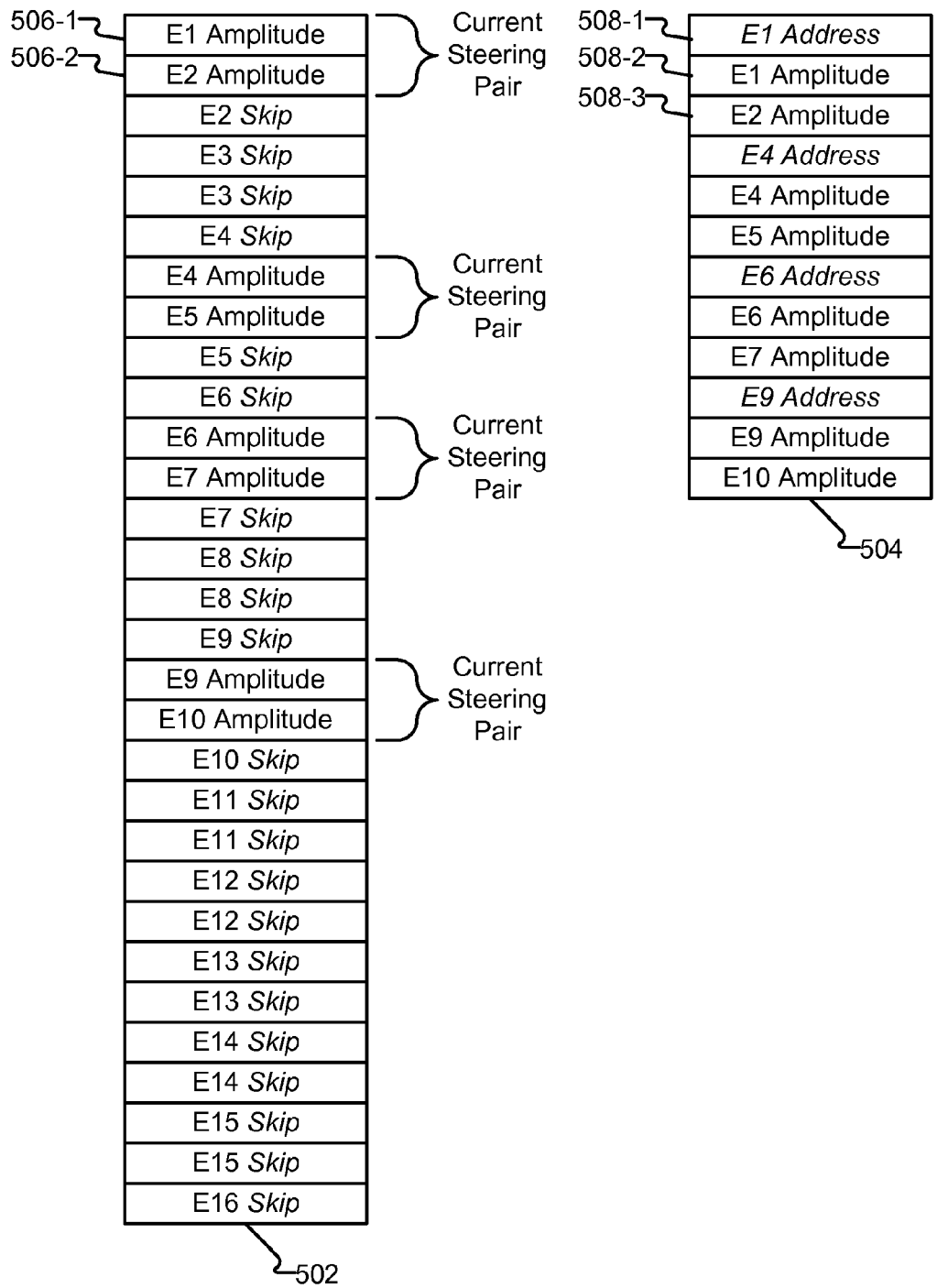
FIG. 5 shows exemplary forward telemetry sequences according to principles described herein.

For the sake of comparison, FIG. 5 shows two possible forward telemetry sequences 502 and 504 that may be realized in accordance with the N of M stimulation strategy that employs current steering between adjacent pairs of electrodes. Forward telemetry sequence 502 corresponds to a fixed electrode addressing heuristic and forward telemetry sequence 504 corresponds to a dynamic electrode addressing heuristic. As illustrated, the forward telemetry sequence 502 corresponding to the fixed electrode addressing heuristic includes two data words for each possible current steering pair (i.e., two amplitude words that specify the amplitude of the stimulation pulses to be applied by way of the two electrodes included in each possible current steering pair). Each data word has its own transmission time slot. To illustrate, with respect to the current steering pair of electrodes E1 and E2, forward telemetry sequence 502 includes a first data word 506-1 that specifies an amplitude for one or more stimulation pulses to be applied by way of electrode E1 and a second data word 506-2 that specifies an amplitude for one or more stimulation pulses to be applied by way of electrode E2.

Because there are sixteen total electrodes, there are fifteen possible current steering pairs. Hence, forward telemetry sequence 502 is required to include thirty data words that occupy thirty total transmission time slots, regardless of the number of current steering pairs actually stimulated during the stimulation frame. To illustrate, in the example of FIG. 5, only four current steering pairs (i.e., electrodes E1 and E2, E4 and E5, E6 and E7, and E9 and E10) are stimulated during the stimulation frame. However, because the order of stimulation is fixed, sound processor 104 is required to include a "skip" command in each transmission time slot during which an amplitude word is not transmitted.

In contrast, forward telemetry sequence 504 (i.e., the forward telemetry sequence that corresponds to a dynamic electrode addressing heuristic), does not have to include any "skip" commands in order to achieve the same result as forward telemetry sequence 502. Rather, forward telemetry sequence 504 includes three data words (e.g., data words 508-1 through 508-3) for each current steering pair that is to be stimulated during the stimulation frame. The first data word (e.g., data word 508-1) in each group of three data words is an address word that includes data representative of a base address of the current steering pair (e.g., an address of the first electrode included in the current steering pair). The second and third data words (e.g., data words 508-2 and 508-3) in each group of three data words are amplitude data words that specify the amplitudes of the stimulation pulses to be applied by way of each electrode included in the current steering pair. To illustrate, data word 508-1 is an address word specifying a base address of the current steering pair of electrodes E1 and E2 and data words 508-2 and 508-3 are amplitude data words that specify the amplitudes of the stimulation pulses to be applied by way of electrodes E1 and E2.

As illustrated in FIG. 5, forward telemetry sequence 504 only requires twelve total data words during the stimulation frame compared to the thirty total data words that are required by forward telemetry sequence 502. This represents a one-hundred fifty percent improvement in overall stimulation rate compared to the fixed electrode addressing heuristic.

It will be recognized that because sound processor 104 may specify any address in each address word included in forward telemetry sequence 504, the order in which the electrodes are addressed may be dynamically modified during a stimulation frame.

To facilitate processing of a dynamically determined forward telemetry sequence, such as forward telemetry sequence 504, processing facility 306 of cochlear implant 108 may be configured to distinguish between address words and amplitude words. This may be realized in any suitable manner. For example, processing facility 306 may reference the entries included within pulse table 412, which may each specify an order in which address words and amplitude words are received.

Figure 6:
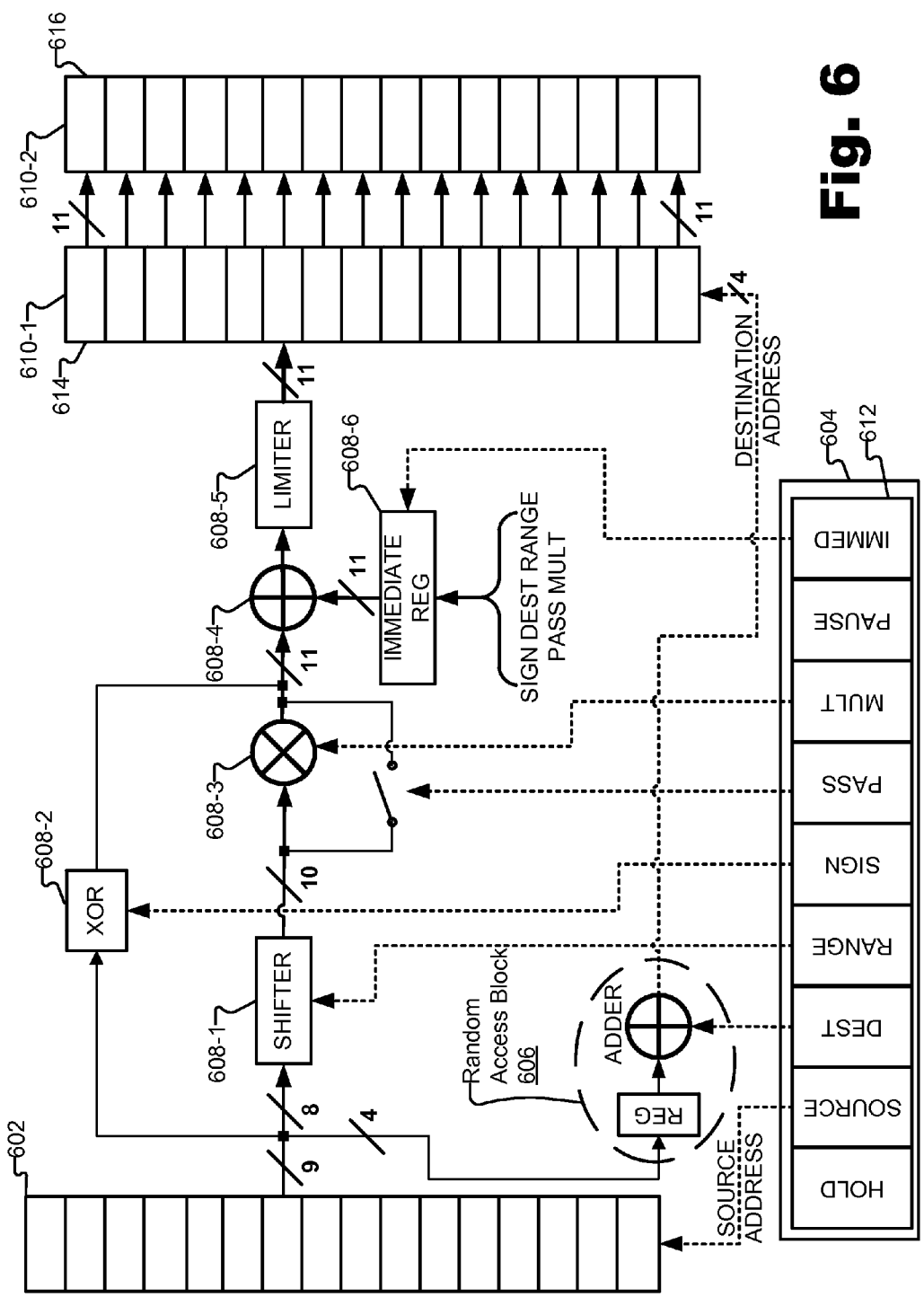
FIG. 6 shows an exemplary implementation of a processing facility of a cochlear implant according to principles described herein.

To illustrate, FIG. 6 shows an exemplary implementation of processing facility 306 of cochlear implant 108. In particular, FIG. 6 shows various components that may be included in cochlear implant 108 and an exemplary data path for data words received and processed by cochlear implant 108. Various features of FIG. 6 are described more fully in the above-referenced U.S. Pat. No. 6,219,580.

As shown in FIG. 6, cochlear implant 108 may include an amplitude frame memory 602, a pulse table memory 604, a random access block 606, amplitude processing circuitry 608 (e.g., components 608-1 through 608-6), and digital-to-analog converter ("DAC") buffers 610-1 and 610-2. Cochlear implant 108 may further include control circuitry (not shown) configured to control an operation of each of these components. Each of these components will be briefly described.

Amplitude frame memory 602 may be configured to maintain a plurality of data words received from sound processor 104 by way of a forward-telemetry link (e.g., communication link 114). For example, amplitude frame memory 602 may be configured to maintain the data words included in forward telemetry sequence 504.

Pulse table memory 604 may be configured to maintain data representative of a plurality of pulse table entries (e.g., pulse table entry 612) that define a stimulation strategy used by cochlear implant 108. Each pulse table entry 612 may include a plurality of fields. For example, as shown in FIG. 6, each pulse table entry 612 may include, among others, a source field, a destination field, and a range field. As will be described below, the source field selects a data word from amplitude frame memory 602 for processing, the destination field is used by random access block 604 to assist in determining an electrode address associated with the data word, and the range field may be used to determine whether the data word is an address word or an amplitude word.

In some examples, sound processor 104 and/or any other external device may be configured to modify and/or load a new pulse table into pulse table memory 604. In this manner, a modified or new stimulation strategy may be employed by cochlear implant system 100.

Figure 7:
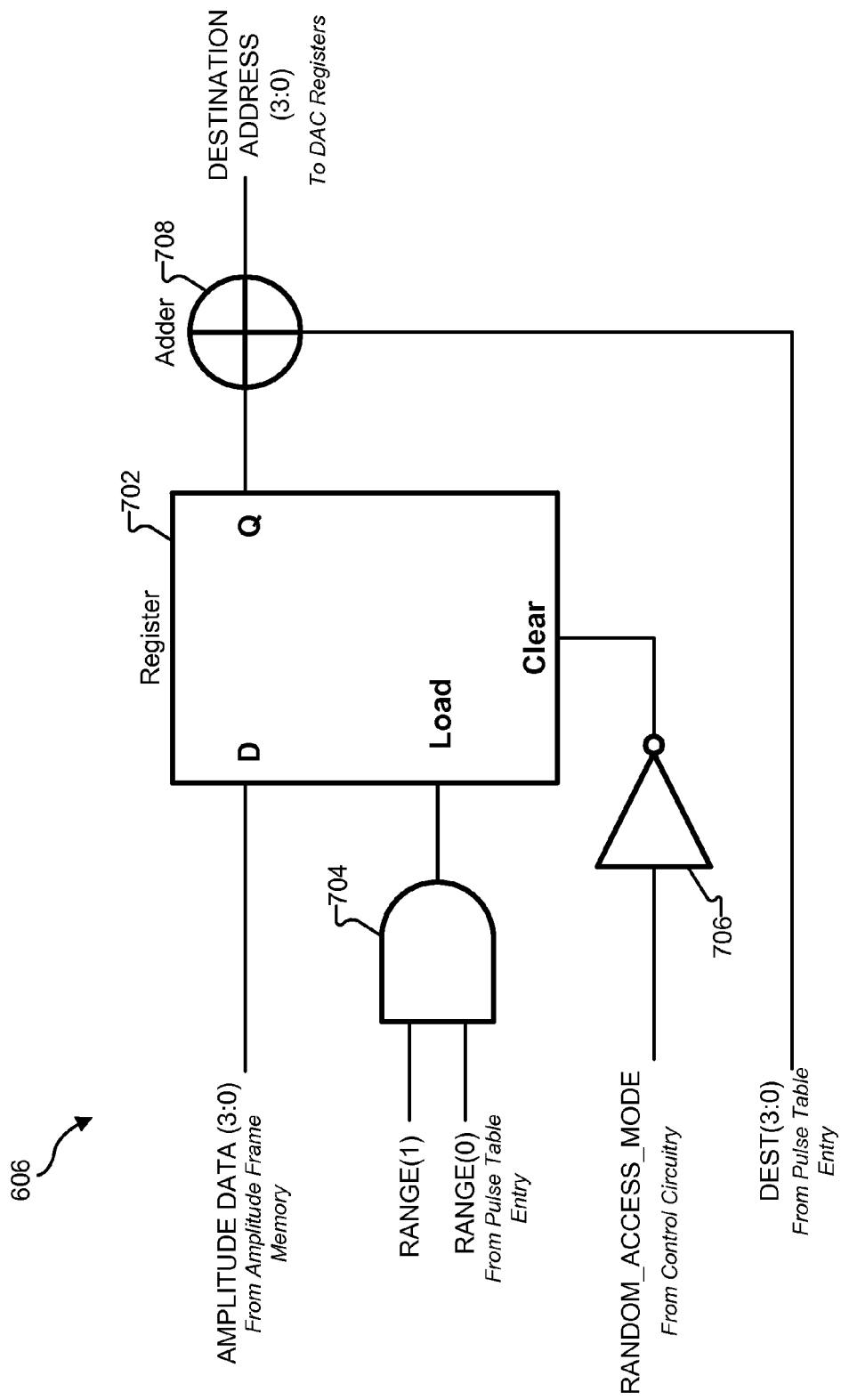
FIG. 7 shows exemplary components that may be included in a random access block according to principles described herein.

Random access block 606 is configured to facilitate dynamic addressing (i.e., selection) of an electrode by way of which a stimulation pulse is to be applied during a time slot of a stimulation frame. FIG. 7 shows exemplary components that may be included in random access block 606. As shown, random access block 606 may include a register 702, an AND gate 704, a NOR gate 706, and an adder 708 coupled one to another as shown in FIG. 7. Exemplary manners in which these components facilitate dynamic addressing (i.e., selection) of an electrode by way of which a stimulation pulse is to be applied during a time slot of a stimulation frame will be described below.

Returning to FIG. 6, amplitude processing circuitry 608 may be configured to facilitate determination of an amplitude of a stimulation pulse that is to be applied by way of an addressed electrode during a particular time slot of a stimulation frame. This may be performed in any suitable manner as may serve a particular implementation.

DAC buffers 610-1 and 610-2 may each include a DAC register (e.g., DAC registers 614 and 616) associated with each electrode 112 in cochlear implant system 100. Data representative of amplitudes of stimulation pulses to be applied by way of a particular electrode included in electrodes 112 may accordingly be stored within a register associated with the particular electrode. In some examples, DAC buffer 610-1 is loaded serially as each data word in amplitude frame memory 602 is processed. At the end of each update interval, the contents of all of the registers included in DAC buffer 610-1 are clocked into DAC buffer 610-2 so that all DACs (i.e., current sources) are updated simultaneously.

Various examples of processing a dynamically determined forward telemetry sequence will now be described with reference to the components described in connection with FIGS. 6-7.

In some examples, a forward telemetry sequence provided by sound processor 104 may include two data words per electrode that is to be stimulated during a stimulation frame. In this case, the pulse table maintained in pulse table memory 604 may specify that every other data word received by cochlear implant 108, beginning with the first data word received, is an address word. Likewise, the pulse table may specify that every other data word received by cochlear implant 108, beginning with the second data word received, is an amplitude word. This may be realized in any suitable manner. For example, a value in the range field of each pulse table entry may specify whether its corresponding data word is an address word or an amplitude word.

To illustrate, the range field in each pulse table entry (e.g., pulse table entry 612) may be a two-bit field. If both bits are "one" (i.e., a binary value of "11"), processing facility 306 (which, in some instances, may be implemented by control circuitry included in cochlear implant 108) may determine that the pulse table entry's corresponding data word is an address word. Any other value in the range field may indicate that the pulse table entry's corresponding data word is an amplitude word. Hence, upon receipt of a first data word, processing facility 306 may determine, based on a value in the range field included in a first pulse table entry, that the first data word is an address word associated with a particular electrode. Likewise, upon receipt of a second data word, processing facility 306 may determine, based on a value in the range field included in a second pulse table entry, that the second data word is an amplitude word associated with the particular electrode.

Once processing facility 306 has determined that the first data word is an address word, processing facility 306 may use the first data word to dynamically determine an address of an electrode by which a stimulation pulse (i.e., one or more stimulation pulses) is be applied during a particular time slot of a stimulation frame. For example, processing facility 306 may direct random access block 606 to extract data (e.g., four bits) representative of the address of the electrode and store the data representative of the address within register 702. As will be described below, the data stored within register 702 may be used to select a particular register included within DAC buffer 610-1 that corresponds to the electrode associated with the address.

Processing facility 306 may subsequently use the second data word to determine, in accordance with instructions included in a second pulse table entry, an amplitude of the stimulation pulse that is to be applied by way of the electrode having the address indicated by the first data word (e.g., by processing the second data word with amplitude processing circuitry 608). Processing facility 306 may then load data representative of the determined amplitude into a DAC register (e.g., DAC register 614) of DAC buffer 610-1 that has an address that matches the address indicated by the first data word.

Processing facility 306 may select a particular DAC register into which the data representative of the determined amplitude based on a "destination address" output (shown in FIG. 7) of random access block 606. As shown in FIG. 7, the destination address output may be derived by summing the data stored within register 702 with an offset value included in a destination field of the second pulse table entry. Because this particular stimulation strategy only stimulates a single electrode during each time slot of the stimulation frame, the offset value included in the destination field of the second pulse table entry is zero. Hence, the destination address output is equivalent to the address data stored in register 702.

After the amplitude data has been loaded into the DAC register of DAC buffer 610-1, the amplitude data may be transferred to a corresponding DAC register (e.g., DAC register 616) included in DAC buffer 610-2. Processing facility 306 may subsequently direct stimulation facility 304 to generate and apply the stimulation pulse having the determined amplitude by way of the electrode associated with the DAC register included in DAC buffer 610-2 in accordance with the amplitude data stored within the DAC register included in DAC buffer 610-2.

As another example, a forward telemetry sequence provided by sound processor 104 may be associated with an N of M stimulation strategy that employs current steering between adjacent pairs of electrodes. For example, the forward telemetry sequence may be similar to forward telemetry sequence 504 in that it includes three data words for each current steering pair that is to be stimulated during a particular stimulation frame. In this case, the pulse table maintained in pulse table memory 604 may specify that every third data word received by cochlear implant 108, beginning with the first data word received, is an address word representative of a base address of the current steering pair. Likewise, the pulse table may specify that the two data words immediately following each address word as received by cochlear implant 108 are amplitude words corresponding to the two electrodes in each current steering pair. This may be realized in any suitable manner. For example, as described above, the range field in each pulse table entry (e.g., pulse table entry 612) may be a two-bit field. If both bits are "one" (i.e., a binary value of "11"), processing facility 306 may determine that the pulse table entry's corresponding data word is an address word. Any other value in the range field may indicate that the pulse table entry's corresponding data word is an amplitude word.

Once processing facility 306 has determined that the first data word in a group of three data words is an address word, processing facility 306 may use the first data word to dynamically determine a base address of the electrode pair. For example, as described above, processing facility 306 may direct random access block 606 to extract data (e.g., four bits) representative of the base address store the data representative of the base address within register 702.

Processing facility 306 may subsequently use the second and third data words to determine an amplitude of the stimulation pulses that are to be applied by way of the two electrodes included in the current steering pair. In so doing, processing facility 306 may determine which electrode included in the current steering pair is associated with each of the determined amplitudes based on the offset values included in the destination fields of the second and third pulse table entries. For example, the second pulse table entry may have an offset value of zero and the second pulse table entry may have an offset value of one. In this manner, the destination address used for the amplitude data associated with the second word is the base address and the destination address used for the amplitude data associated with the third word is the base address summed with the offset address.

While the above example is in the context of current steering between adjacent pairs of electrode, it will be recognized that the systems and methods described herein may also be used in the context of other stimulation strategies that use more than two adjacent and/or non-adjacent electrodes. For example, the systems and methods described herein may be used in the context of tri-polar, phased-array, and/or other multipolar stimulation strategies.

In some examples, processing facility 306 may disable random access block 606 by providing a "random_access_mode" signal to inverter 706 shown in FIG. 7. As shown, inverter 706 is coupled to a "clear" input port of register 702. In this manner, random access block 606 may be disabled before a particular stimulation session that does not require the use of random access block 606.

Figure 8:
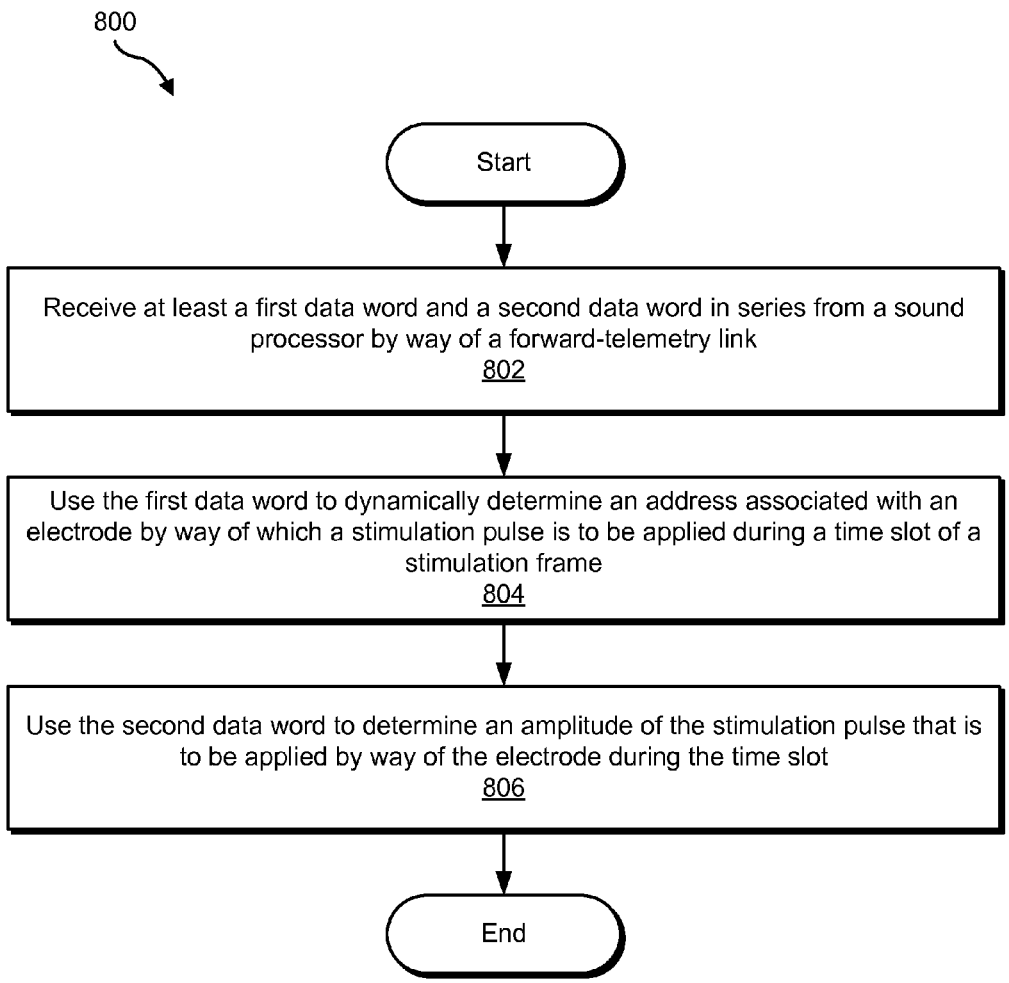
FIG. 8 illustrates an exemplary random-access addressing method according to principles described herein.

FIG. 8 illustrates an exemplary random-access addressing method 800. While FIG. 8 illustrates exemplary steps according to one embodiment, other embodiments may omit, add to, reorder, and/or modify any of the steps shown in FIG. 8. One or more of the steps shown in FIG. 8 may be performed by any component or combination of components of cochlear implant 108.

In step 802, a cochlear implant receives at least a first data word and a second data word in series from a sound processor by way of a forward-telemetry link. Step 802 may be performed in any of the ways described herein.

In step 804, the cochlear implant uses the first data word to dynamically determine an address associated with an electrode by way of which a stimulation pulse is to be applied during a time slot of a stimulation frame. Step 804 may be performed in any of the ways described herein.

In step 806, the cochlear implant uses the second data word to determine an amplitude of the stimulation pulse that is to be applied by way of the electrode during the time slot of the stimulation frame. Step 806 may be performed in any of the ways described herein.

In some examples, a cochlear implant may include 1) an amplitude frame memory that maintains a plurality of data words received from a sound processor by way of a forward-telemetry link, the plurality of data words comprising at least a first data word and a second data word, 2) a pulse table memory that maintains data representative of a plurality of pulse table entries that define a stimulation strategy used by the cochlear implant, the plurality of pulse table entries comprising at least a first pulse table entry and a second pulse table entry, 3) a random access block that facilitates dynamic selection of an electrode by way of which a stimulation pulse is to be applied during a time slot of a stimulation frame, 4) amplitude processing circuitry that facilitates determination of an amplitude of the stimulation pulse that is to be applied by way of the electrode during the time slot, and 5) control circuitry communicatively coupled to the amplitude frame memory, the pulse table memory, the random access block, and the amplitude processing circuitry. The control circuitry may 1) determines, based on a value in a range field included in the first pulse table entry, that the first data word is an address word, 2) direct, based on the determination that the first data word is an address word, the random access block to extract data representative of an address associated with the electrode from the first data word and store the data representative of the address within a register included within the random access block, 3) determine, based on a value in a range field included in the second pulse table entry, that the second data word is an amplitude word, 4) direct, based on the determination that the second data word is an amplitude word, the amplitude processing circuitry to use the second data word to generate amplitude data representative of the amplitude of the stimulation pulse that is to be applied by way of the electrode during the time slot, and 5) direct the amplitude processing circuitry to load the amplitude data into a DAC register that has an address that matches the address stored within the register included within the random access block.

In some examples, the amplitude frame memory may further maintain a third data word and the pulse table further comprises a third pulse table entry. In these examples, the control circuitry may 1) determine, based on a value in a range field included in the third pulse table entry, that the third data word is an amplitude word, 2) determine, in response the determination that the third data word is an amplitude word and based on an offset value in a destination field included in the third pulse table entry, an additional address associated with an additional electrode by way of which an additional stimulation pulse is to be applied during the time slot, 3) direct, in response the determination that the third data word is an amplitude word, the amplitude processing circuitry to use the third data word to generate additional amplitude data representative of an amplitude of the additional stimulation pulse that is to be applied by way of the additional electrode during the time slot, and 4) direct the amplitude processing circuitry to load the additional amplitude data into a DAC register that has an address that matches the additional address.

It will be recognized that additional data may be included in the forward telemetry sequence in accordance with the systems and methods described herein. For example, sound processor 104 may include a data word in the forward telemetry sequence that specifies a pulse width of each stimulation pulse that is to be applied by way of electrodes 112.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A cochlear implant comprising:
a communication facility configured to receive at least a first data word, a second data word, and a third data word in series from a sound processor by way of a forward-telemetry link;
a processing facility communicatively coupled to the communication facility and configured to
maintain a pulse table comprising a first pulse table entry, a second pulse table entry, and a third pulse table entry,
determine, based on a value in a range field included in the first pulse table entry, that the first data word is an address word,
determine, based on a value in a range field included in the second pulse table entry, that the second data word is an amplitude word,
determine, based on a value in a range field included in the third pulse table entry, that the third data word is an additional amplitude word,
use, in response to the determination that the first data word is the address word, the first data word to dynamically determine an address associated with an electrode by way of which a stimulation pulse is to be applied during a time slot of a stimulation frame,
use, in response to the determination that the second data word is the amplitude word, the second data word to determine an amplitude of the stimulation pulse that is to be applied by way of the electrode during the time slot,
determine, in response to the determination that the third data word is the additional amplitude word and based on an offset value in a destination field included in the third pulse table entry, an additional address associated with an additional electrode by way of which an additional stimulation pulse is to be applied during the time slot, and
use, in response to the determination that the third data word is the additional amplitude word, the third data word to determine an amplitude of the additional stimulation pulse that is to be applied by way of the additional electrode during the time slot.

2. The cochlear implant of claim 1, wherein the processing facility is further configured to:
load data representative of the determined amplitude of the stimulation pulse into a first digital-to-analog converter ("DAC") register that has the address associated with the electrode; and
load data representative of the determined amplitude of the additional stimulation pulse into a second DAC register that has the additional address associated with the additional electrode.

3. The cochlear implant of claim 2, wherein the processing facility is further configured to direct a stimulation facility to:
generate and apply the stimulation pulse by way of the electrode during the time slot in accordance with the data loaded into the first DAC register; and
generate and apply the additional stimulation pulse by way of the additional electrode during the time slot in accordance with the data loaded into the second DAC register.

4. The cochlear implant of claim 3, wherein the processing facility is configured to direct the stimulation facility to generate and apply the stimulation pulse and the additional stimulation pulse in accordance with a current steering strategy.

5. The cochlear implant of claim 1, wherein the processing facility is configured to determine the additional address associated with the additional electrode by adding the offset value in the destination field included in the third pulse table entry to the address associated with the electrode.

6. The cochlear implant of claim 1, wherein the processing facility is further configured to load data representative of the determined amplitude into a digital-to-analog converter ("DAC") register that has the address associated with the electrode.

7. The cochlear implant of claim 6, wherein the processing facility is further configured to direct a stimulation facility to generate and apply the stimulation pulse having the determined amplitude by way of the electrode during the time slot in accordance with the data loaded into the DAC register that has the address associated with the electrode.

8. The cochlear implant of claim 1, wherein the processing facility is configured to use the first data word to dynamically determine the address associated with the electrode by loading a predetermined number of bits included in the first data word and representative of the address into a register.

9. The cochlear implant of claim 8, wherein the predetermined number of bits is four.

10. A cochlear implant comprising:
an amplitude frame memory that maintains a plurality of data words received from a sound processor by way of a forward-telemetry link, the plurality of data words comprising at least a first data word, a second data word, and a third data word;

a pulse table memory that maintains data representative of a plurality of pulse table entries that define a stimulation strategy used by the cochlear implant, the plurality of pulse table entries comprising at least a first pulse table entry, a second pulse table entry, and a third pulse table entry;

a random access block that facilitates dynamic selection of an electrode by way of which a stimulation pulse is to be applied during a time slot of a stimulation frame;

amplitude processing circuitry that facilitates determination of an amplitude of the stimulation pulse that is to be applied by way of the electrode during the time slot; and control circuitry communicatively coupled to the amplitude frame memory, the pulse table memory, the random access block, and the amplitude processing circuitry and that determines, based on a value in a range field included in the first pulse table entry, that the first data word is an address word, directs, based on the determination that the first data word is an address word, the random access block to extract data representative of an address associated with the electrode from the first data word and store the data representative of the address within a register included within the random access block, determines, based on a value in a range field included in the second pulse table entry, that the second data word is an amplitude word, directs, based on the determination that the second data word is the amplitude word, the amplitude processing circuitry to use the second data word to generate amplitude data representative of the amplitude of the stimulation pulse that is to be applied by way of the electrode during the time slot, directs the amplitude processing circuitry to load the amplitude data into a digital-to-analog converter ("DAC") register that has an address that matches the address stored within the register included within the random access block, determines, based on a value in a range field included in the third pulse table entry, that the third data word is an additional amplitude word, determines, in response the determination that the third data word is the additional amplitude word and based on an offset value in a destination field included in the third pulse table entry, an additional address associated with an additional electrode by way of which an additional stimulation pulse is to be applied during the time slot, directs, in response the determination that the third data word is the additional amplitude word, the amplitude processing circuitry to use the third data word to generate additional amplitude data representative of an amplitude of the additional stimulation pulse that is to be applied by way of the additional electrode during the time slot, and directs the amplitude processing circuitry to load the additional amplitude data into a DAC register that has an address that matches the additional address.

11. The cochlear implant of claim 10, wherein the control circuitry determines the additional address associated with the additional electrode by directing the random access block to add the offset value in the destination field included in the third pulse table entry to the address stored in the register.

12. The cochlear implant of claim 10, wherein the control circuitry is further configured to direct a DAC associated with the DAC register to generate the stimulation pulse having the determined amplitude by way of the electrode during the time slot in accordance with the amplitude data loaded into the DAC register.

13. A method comprising:
receiving, by a cochlear implant, at least a first data word, a second data word, and a third data word in series from a sound processor by way of a forward-telemetry link;
maintaining, by the cochlear implant, a pulse table comprising a first pulse table entry, a second pulse table entry, and a third pulse table entry;
determining, by the cochlear implant based on a value in a range field included in the first pulse table entry, that the first data word is an address word;
determining, by the cochlear implant based on a value in a range field included in the second pulse table entry, that the second data word is an amplitude word;
determining, by the cochlear implant based on a value in a range field included in the third pulse table entry, that the third data word is an additional amplitude word;
using, by the cochlear implant in response to the determining that the first data word is the address word, the first data word to dynamically determine an address associated with an electrode by way of which a stimulation pulse is to be applied during a time slot of a stimulation frame; and
using, by the cochlear implant in response to the determining that the second data word is the amplitude word, the second data word to determine an amplitude of the stimulation pulse that is to be applied by way of the electrode during the time slot;
determining, by the cochlear implant in response the determining that the third data word is the additional amplitude word and based on an offset value in a destination field included in the third pulse table entry, an additional address associated with an additional electrode by way of which an additional stimulation pulse is to be applied during the time slot; and
using, by the cochlear implant in response the determining that the third data word is the additional amplitude word, the third data word to determine an amplitude of the additional stimulation pulse that is to be applied by way of the additional electrode during the time slot.

14. The method of claim 13, further comprising:
loading, by the cochlear implant, data representative of the determined amplitude of the stimulation pulse into a first digital-to-analog converter ("DAC") register that has the address associated with the electrode; and
loading, by the cochlear implant, data representative of the determined amplitude of the additional stimulation pulse into a second DAC register that has the additional address associated with the additional electrode.

15. The method of claim 14, further comprising:
generating and applying, by the cochlear implant, the stimulation pulse by way of the electrode during the time slot in accordance with the data loaded into the first DAC register; and
generating and applying, by the cochlear implant, the additional stimulation pulse by way of the additional electrode during the time slot in accordance with the data loaded into the second DAC register.

16. The method of claim 15, wherein the generating and applying of the stimulation pulse and the additional stimulation pulse is performed in accordance with a current steering strategy.

17. The method of claim 13, further comprising determining, by the cochlear implant, the additional address associated with the additional electrode by adding the offset value in the destination field included in the third pulse table entry to the address associated with the electrode.

18. The method of claim 13, further comprising loading, by the cochlear implant, data representative of the determined amplitude into a digital-to-analog converter ("DAC") register that has the address associated with the electrode.

19. The method of claim 18, further comprising generating and applying, by the cochlear implant, the stimulation pulse having the determined amplitude by way of the electrode during the time slot in accordance with the data loaded into the DAC register that has the address associated with the electrode.

20. The method of claim 13, further comprising using, by the cochlear implant, the first data word to dynamically determine the address associated with the electrode by loading a predetermined number of bits included in the first data word and representative of the address into a register.

* * * * *